United States Patent
Ajay

(10) Patent No.: US 11,385,212 B2
(45) Date of Patent: Jul. 12, 2022

(54) SMOKE DETECTION SAMPLE POINT

(71) Applicant: Honeywell International Inc., Charlotte, NC (US)

(72) Inventor: Kemal Ajay, Mount Waverley (AU)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 17/032,661

(22) Filed: Sep. 25, 2020

(65) Prior Publication Data
US 2022/0099644 A1    Mar. 31, 2022

(51) Int. Cl.
| | | |
|---|---|---|
| *G01N 33/00* | (2006.01) |
| *F16K 15/03* | (2006.01) |
| *G01N 1/24* | (2006.01) |
| *G08B 17/117* | (2006.01) |
| *G01N 1/22* | (2006.01) |

(52) U.S. Cl.
CPC ......... *G01N 33/0036* (2013.01); *F16K 15/03* (2013.01); *G01N 1/2205* (2013.01); *G01N 1/2273* (2013.01); *G01N 1/24* (2013.01); *G01N 33/0011* (2013.01); *G08B 17/117* (2013.01)

(58) Field of Classification Search
CPC .... G01N 33/0036; G01N 1/2273; G01N 1/24; G01N 33/0011; G01N 1/2205; F16K 15/03; G08B 17/117
USPC ...................................................... 73/31.02
See application file for complete search history.

(56) References Cited

U.S. PATENT DOCUMENTS 3,765,247 A * 10/1973 Riggs ....................... G01N 1/26
                                                                73/863.23
3,767,925 A * 10/1973 Foley, Jr. ........... G01N 23/2073
                                                                250/251

(Continued)

FOREIGN PATENT DOCUMENTS

| CN | 103646490 A | 3/2014 |
|---|---|---|
| WO | 2015071409 A1 | 5/2015 |

OTHER PUBLICATIONS

VESDA-E VEA Sampling Points, xtrails, www.xtralis.com, 2021, 2 pages (Year: 2021).*

(Continued)

*Primary Examiner* — Clayton E. LaBalle
*Assistant Examiner* — Kevin C Butler
(74) *Attorney, Agent, or Firm* — Brooks, Cameron & Huebsch, PLLC

(57) ABSTRACT

Smoke detection sample points and systems are described herein. One smoke detection sample point includes a body; a chamber formed within the body, the chamber having a first aperture, to allow air to pass between an area to be sampled and the chamber, and a second aperture, to allow air to pass between the chamber and a space within a second enclosure; a valve positioned within the chamber; a first enclosure surrounding the body, but allowing the first aperture to pass air between the area to be sampled and the chamber and the second aperture to pass air between the chamber and the space within the second enclosure; and the second enclosure surrounding the first enclosure and having a third aperture, the third aperture allowing the air in the space within the second enclosure to pass between the second enclosure and a tube connected to the second enclosure.

14 Claims, 5 Drawing Sheets

(56) References Cited

U.S. PATENT DOCUMENTS

| | | | | |
|---|---|---|---|---|
| 3,980,997 A * | 9/1976 | Berns | G08B 17/103 | 340/630 |
| 4,155,653 A * | 5/1979 | San Miguel | G01N 21/534 | 250/564 |
| 4,194,191 A * | 3/1980 | Salem | G08B 17/11 | 250/381 |
| 4,238,679 A * | 12/1980 | Macmillan | G08B 17/113 | 250/385.1 |
| 4,294,165 A * | 10/1981 | Bergdahl | A62C 2/08 | 137/253 |
| 4,361,763 A * | 11/1982 | Bryant | G08B 17/113 | 250/381 |
| 4,531,453 A * | 7/1985 | Warman | B60H 3/0608 | 454/139 |
| 4,758,827 A * | 7/1988 | Powers | G08B 17/103 | 116/273 |
| 4,920,263 A * | 4/1990 | Fimian | G01T 1/003 | 250/255 |
| 5,021,250 A * | 6/1991 | Ferguson | B67D 1/00 | 222/1 |
| 5,103,212 A * | 4/1992 | Notarianni | G01N 1/26 | 340/628 |
| 5,501,234 A * | 3/1996 | Hyre | A24F 13/00 | 131/187 |
| 5,665,924 A * | 9/1997 | Cole | G01N 1/26 | 73/863.81 |
| 8,528,385 B2 * | 9/2013 | Raghavendra | F16L 33/2073 | 73/40.5 R |
| 10,161,837 B2 * | 12/2018 | Ajay | G08B 17/113 | |
| 2003/0033890 A1 * | 2/2003 | Rodgers | G01N 1/2211 | 73/863.43 |
| 2005/0087027 A1 * | 4/2005 | Widmer | G01N 1/2258 | 73/863.02 |
| 2005/0183575 A1 * | 8/2005 | Fox | G01N 1/24 | 95/273 |
| 2007/0137318 A1 * | 6/2007 | Desrochers | G01N 1/26 | 73/863.81 |
| 2007/0168140 A1 * | 7/2007 | Knox | G01N 15/06 | 702/45 |
| 2009/0002182 A1 * | 1/2009 | Knox | B01D 46/0043 | 340/628 |
| 2009/0237259 A1 * | 9/2009 | Yokota | G08B 17/113 | 340/628 |
| 2009/0293581 A1 * | 12/2009 | Nadin | G01F 1/704 | 73/1.06 |
| 2010/0199785 A1 * | 8/2010 | Timmis | G01N 1/2214 | 73/863.21 |
| 2010/0206043 A1 * | 8/2010 | Tewarson | G01N 1/26 | 73/23.41 |
| 2010/0328082 A1 * | 12/2010 | Danz | G08B 17/10 | 340/589 |
| 2014/0231531 A1 * | 8/2014 | van der Donk | F23N 5/242 | 237/12 |
| 2015/0096389 A1 * | 4/2015 | Knox | G01N 1/26 | 73/864.34 |
| 2015/0310717 A1 * | 10/2015 | Al-Farra | G08B 17/12 | 340/628 |
| 2016/0238495 A1 | 8/2016 | Joseph | | |
| 2017/0045415 A1 | 2/2017 | Williamson | | |
| 2018/0149559 A1 * | 5/2018 | Williamson | G01N 1/2273 | |
| 2018/0149581 A1 * | 5/2018 | Lo | G01N 21/0303 | |
| 2019/0159830 A1 * | 5/2019 | Horner | A61B 18/1402 | |
| 2019/0201593 A1 * | 7/2019 | Shelton, IV | G05B 19/0428 | |
| 2020/0193791 A1 * | 6/2020 | Gonzales | G08B 29/043 | |
| 2021/0165925 A1 * | 6/2021 | Birnkrant | G06F 30/13 | |
| 2021/0174659 A1 * | 6/2021 | Hartwig | G01N 21/53 | |
| 2021/0270789 A1 * | 9/2021 | Desjardins | G08B 17/06 | |

OTHER PUBLICATIONS

Determining the Effectiveness, Limitations and Operator Response for Very Early Warning Fire Detection Systems in Nuclear Facilities, United States Nuclear Regulatory Commission (U.S.NRC), Dec. 2016, 485 pages (Year: 2016).*

A novel box for aerosol and droplet guarding and evacuation in respiratory infection (BADGER) for COVID-19 and future outbreaks, Scientific Reports, www.nature.com/scientificreports, 2021, 12 pages (Year: 2021).*

European Extended Search Report for related European Application No. 21197821.8, dated Feb. 15, 2022 (9 pgs).

* cited by examiner

SMOKE DETECTION SAMPLE POINT

TECHNICAL FIELD

The present disclosure relates to smoke detection, and in particular, sample point apparatuses for use in smoke detection systems.

BACKGROUND

Some smoke detection systems have a number of sample points spaced around a building that are connected via sampling tubes to a central analysis device that samples air taken from the sample points to determine if smoke or a fire is present in an area of the building. For example, such systems may be referred to as very early smoke detection apparatus (VESDA) systems.

Sample points typically have an apparatus body with a chamber formed therein. The chamber includes a first aperture, to allow air to pass between the area to be sampled and the chamber, and a second aperture to allow air to pass between the chamber and the tube, that is connected at its other end, to a central analysis device. The chamber also includes a one-way valve therein that allows inflow of air from the area to be sampled and restricts the outflow of air from the chamber.

As these systems draw air through the sample point to the central analysis device, the tube may become separated from the sampling chamber or may be damaged in such a way that air leaks into it from spaces other than that intended to be sampled. A condition of disconnection or leak is regarded a fault condition and must be detected and the fault reported to a monitoring system.

In order to check for this fault condition, the system attempts to force air out through the sampling chamber by applying positive pressure with respect to the chamber environment. If the tube is undamaged and is connected fully to the sampling chamber, the flow in the tube is restricted by the one-way valve in the sampling-point chamber. If the system measures the tube outflow to be above a threshold, or if the measured back pressure is low, then the system determines that either there is a leak or that the sampling-point chamber has become partially or fully disconnected from the tube and raises a fault notification to the monitoring device.

Further, in some implementations, an enclosure can be secured around a chamber of the sample point, as shown in FIGS. 3A-3B for the purpose of protecting it. However, if a leak or breach occurs in the protective enclosure, also as shown in FIGS. 3A-3B, air may be sampled from an unintended space shown by 336 in FIG. 3B and is regarded as a fault condition. The current designs of FIGS. 3A and 3B cannot identify that the leak or breach has occurred, as the leak test performed by the central system will pass because the one way valve activates restricting the outward air flow as shown in FIG. 3A. Thus, the breach 334 is not detectable by the central system.

DETAILED DESCRIPTION

Figure 1:
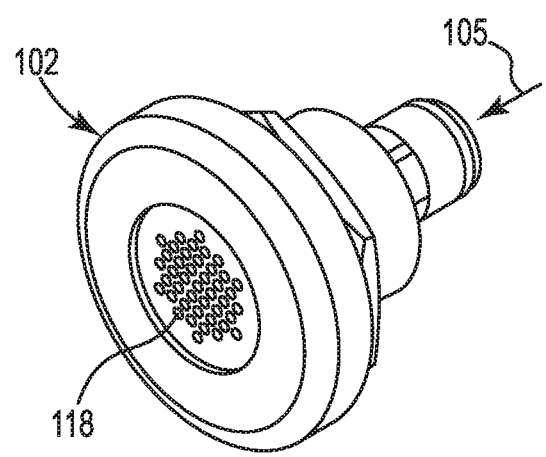
FIG. 1 illustrates an angled perspective view of a prior art sample point.

As discussed above, smoke detection sample points and systems are described herein. Embodiments of the present disclosure allow for the system to reliably test for leaks as described in more detail below.

For example, in one embodiment, a smoke detection sample point includes a body, a first enclosure, and a second enclosure; a chamber formed within the body, the chamber having a first aperture, to allow air to pass between an area to be sampled and the chamber, and a second aperture, to allow air to pass between the chamber and a space within the second enclosure. A valve is also positioned within the chamber.

The first enclosure surrounds the body, but allows the first aperture to pass air between the area to be sampled and the chamber and the second aperture to pass air between the chamber and the space within the second enclosure. The second enclosure surrounds the first enclosure and has a third aperture, the third aperture allows the air in the space within the second enclosure to pass between the second enclosure and a tube connected to the second enclosure. To accomplish this, the first enclosure may also have a first aperture positioned between the first aperture of the body and the area to be sampled and a second aperture positioned between the second aperture of the body and the second enclosure. This embodiment and others will be discussed in more detail with reference to the drawings provided with this disclosure.

In the following detailed description, reference is made to the accompanying drawings that form a part hereof. The drawings show, by way of illustration, how one or more embodiments of the disclosure may be practiced.

These embodiments are described in sufficient detail to enable those of ordinary skill in the art to practice one or more embodiments of this disclosure. It is to be understood that other embodiments may be utilized and that process, computerized, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits. For example, 118 may reference element "18" in FIG. 1, and a similar element may be referenced as 218 in FIG. 2A.

As used herein, "a" or "a number of" something can refer to one or more such things. For example, "a number of apertures" can refer to one or more apertures. As used herein, "a plurality of" means two or more things.

FIG. 1 illustrates an angled perspective view of a prior art sample point. FIG. 1 represents a replaceable smoke detection sample point that can be utilized with embodiments of the present disclosure. The sample point shown provides a unitary body 102 having a first aperture 118, and a second aperture 105. The second aperture 105 is releasably connected to one end of a tube that is connected at its other end to a central analysis device.

Such a smoke detector sample point can, for example, be mounted in the ceiling of a building, such that the end portion of the body 102 having aperture 118 is in an area to be sampled (e.g., area below a ceiling) and the rest of the device is above or in the ceiling. As these sampling devices sometimes get fouled with debris, this device design allows for the sample point to be removed from the tube for inspection of the inside of the tube and the chamber within the body 102. This also allows for easy replacement of the sample point if it cannot be unfouled.

Figure 2A:
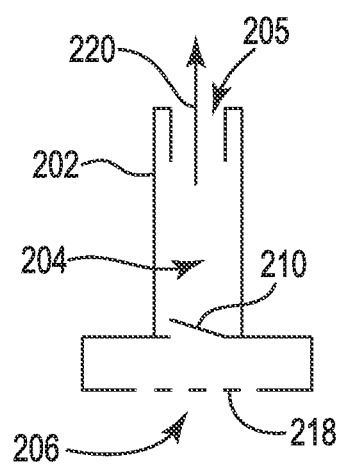
FIG. 2A illustrates a cutaway side view of a prior art sample point wherein the valve is in an open (inflow) position.
Figure 2B:
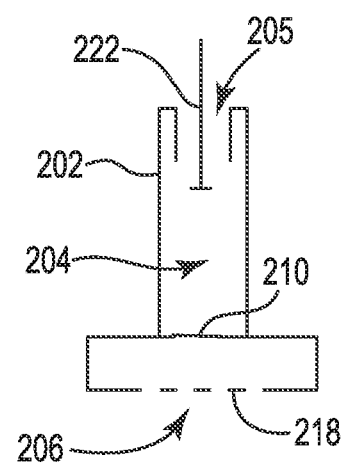
FIG. 2B illustrates a cutaway side view of a prior art sample point wherein the valve is in a closed (outflow) position.

FIG. 2A illustrates a cutaway side view of a prior art sample point wherein the valve is in an open (inflow) position. FIG. 2B illustrates a cutaway side view of a prior art sample point wherein the valve is in a closed (outflow) position.

FIGS. 2A and 2B represent a cutaway view of a sample point that is similar to that shown in FIG. 1, but is shown in two different states of operation. For example, the sample point of FIGS. 2A and 2B includes a body 202 having a chamber 204 formed therein and having a first aperture 218 and a second aperture 205.

The first aperture 218 is positioned such that it is in an area where the air 206 is to be sampled. In operation, this air 206 will be drawn into the sample point via aperture 218 into chamber 204 and then it will be passed into a tube via aperture 205 where it will travel to the central analysis device.

To accomplish this, the second aperture 205 is sized for the insertion and affixation of the end of a tube having a similarly sized diameter to be frictionally fastened or fastened by some other mechanism, such as an adhesive material to the body 202. The aperture should be sized and/or affixed such that leakage of air between the tube and the body is minimized or eliminated.

FIGS. 2A and 2B illustrate that a valve 210 is located within the chamber 204. This valve can be a one-way valve, as shown, where the valve 210 is in an open position and air 220 flows toward the central analysis device during normal operation of the sample point. As used herein, normal operation is when the sample point is attempting to sense smoke in the air 206 being drawn into the sample point 202, via first aperture 218.

When checking for leaks or performing maintenance operations, the flow of air may be reversed. In such instances, air flows into the chamber via second aperture 205, but closes the valve, thereby slowing or substantially stopping the air from flowing, as represented at 222.

To check for leaks, the central analysis device senses the restricted outward air flow for a given air pressure (due to the closure of the valve) and determines that there are no leaks, based on the air flow characteristics (flow versus pressure) measured being within an acceptable range indicating no leaks are present. If the outward air flow remains above a limit for a given pressure, or if the required pressure cannot be achieved, the central analysis device determines that a leak is present somewhere in either: the tube, the body 202, or the valve 210.

Such systems work well in most applications, but in some, such as prisons, hospitals, and schools, it may be desirable to position the entire body in or above the ceiling, for example, to avoid tampering by occupants of the space to be sampled. However, the problem with positioning the entire body in or above the ceiling is that the air drawn in to the sample point will likely be air from above the ceiling and not air from the area to be sampled, which renders the sample point ineffective. FIGS. 3 and 4 show one such design for overcoming this problem for such placement.

Figure 3A:
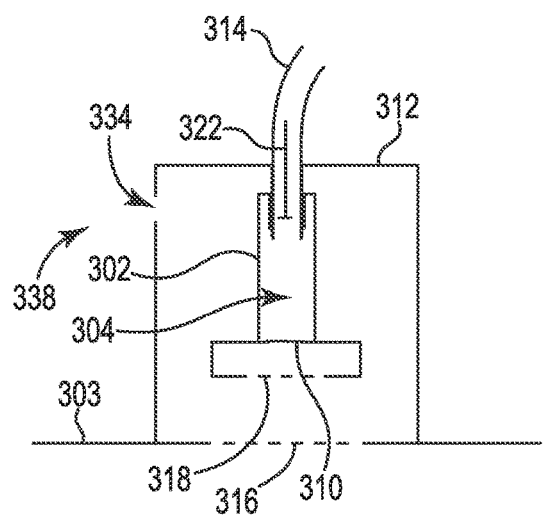
FIG. 3A illustrates a cutaway side view of a prior art sample point having an enclosure wherein the valve is in a closed (out flow) position.
Figure 3B:
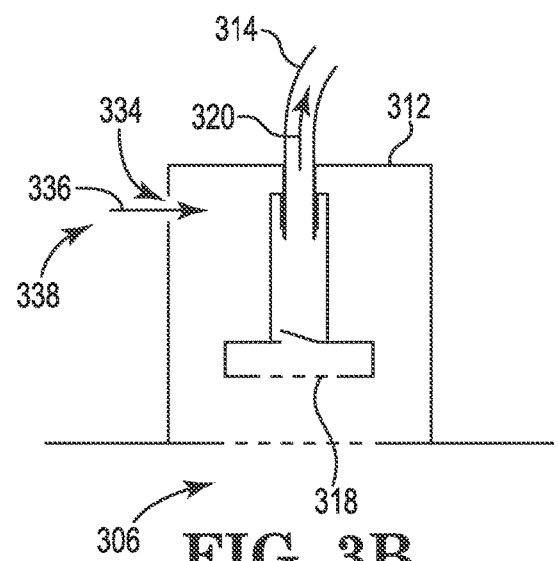
FIG. 3B illustrates a cutaway side view of a prior art sample point having an enclosure wherein the valve is in an open (inflow) position.

FIG. 3A illustrates a cutaway side view of a prior art sample point having an enclosure wherein the valve is in a closed (out flow) position. FIG. 3B illustrates a cutaway side view of a prior art sample point having an enclosure wherein the valve is in an open (inflow) position.

The embodiment of FIGS. 3A and 3B resolves the issue of sampling the air above the ceiling rather than the air in the area to be sampled by positioning an enclosure around the sample point body. In FIGS. 3A and 3B, the body 302 is positioned above ceiling 303, but to reduce or eliminate the sampling of air 338 from above the ceiling, an enclosure 312 is positioned around the body 302. The enclosure surrounds the body 302 on at least five sides (in an XYZ axial space) to restrict air flow from those sides, but allows air flow. for example, through the remaining side (below the body) via an aperture 316. In this manner, air from the area to be sampled can be sampled (through apertures 316 of the enclosure 312 (this aperture can be formed in the ceiling material or, alternatively, from the material forming the rest of the enclosure) and 318 of the body 302) by being drawn into the chamber 304, through the open valve 310, and then to the tube 314 (at 320) to the central analysis device connected to the tube.

However, if a breach, such as hole 334, is present in the enclosure (e.g., through puncture due to tampering) then air 338 enters the enclosure and mixes with the air from the area to be sampled 306. This may distort the analysis of the area to be sampled.

Further, during a leak check, when air flow is reversed (as shown in FIG. 3A), and the flow is restricted as represented at 322, the system will still register that there is no leak, as the leak is outside of the valve 310 and an air-flow versus pressure value that is characteristic of an operational system with no leaks will be provided. This can be problematic when, as shown in FIG. 3B, air from both, the area to be sampled 306 and the area above the ceiling 338 (air indicated at 336), are drawn into aperture 318 and the air 320 passes through tube 314 and to the central analysis device.

Figure 4A:
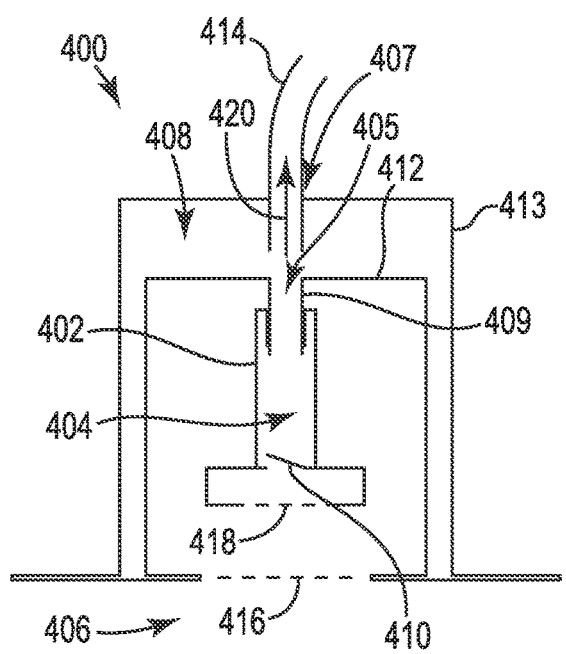
FIG. 4A illustrates a cutaway side view of a sample point according to an embodiment of the present disclosure wherein the valve is in an open (inflow) position.
Figure 4B:
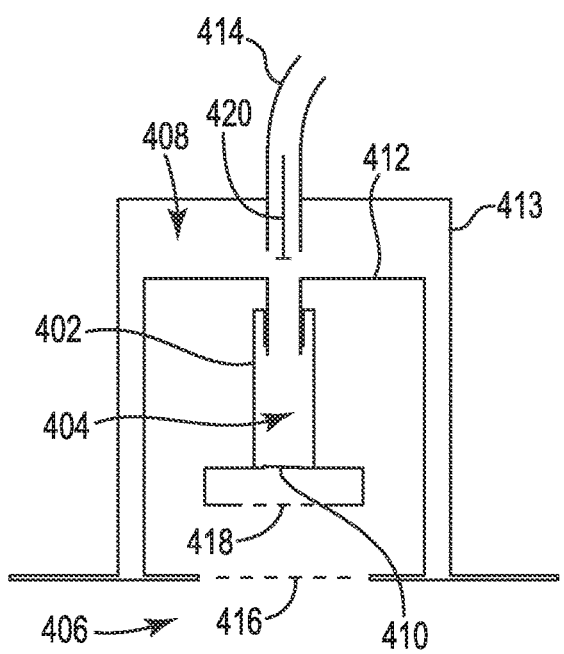
FIG. 4B illustrates a cutaway side view of a sample point according to an embodiment of the present disclosure wherein the valve is in a closed (outflow) position.

Embodiments of the present disclosure overcome this leak detection issue as discussed in more detail below. FIG. 4A illustrates a cutaway side view of a sample point according to an embodiment of the present disclosure wherein the valve is in an open (inflow) position. FIG. 4B illustrates a cutaway side view of a sample point according to an embodiment of the present disclosure, wherein the valve is in a closed (outflow) position.

In FIGS. 4A and 4B, an embodiment is shown that is constructed according to the present disclosure and resolves the leakage issues discussed above. In this embodiment, the sample point includes a second enclosure that surrounds the first enclosure and the attachment location of the tube is changed. In this manner, the system can identify leaks that would introduce air from above the ceiling into the system.

In an embodiment such as FIGS. 4A and 4B, the sample point 400 includes a body 402 is mounted inside a first enclosure 412 and the first enclosure is surrounded by a second enclosure. This construction can be unitary, meaning that, once constructed, the body cannot be removed from the first enclosure and the second enclosure cannot be removed from the first enclosure. In this manner, the entire unitary body and dual enclosure combination may need to periodically be replaced, but the potential for leaks will be minimized.

The body 402 includes a chamber 404 formed within the body, the chamber has a first aperture 418, to allow air to pass between an area to be sampled 406 and the chamber 404, and a second aperture 405, to allow air to pass between the chamber 404 and a space within a second enclosure 408. The chamber 404 also includes a valve 410 positioned therein.

The first enclosure 412 surrounds the body 402, but allows the first aperture 418 to pass air between the area to be sampled 406 and the chamber 404. The second aperture 405 passes air between the chamber 404 and the space within the second enclosure 408.

The second enclosure 413 surrounds the first enclosure 412 and has a third aperture 407. The third aperture 407 allows the air in the space within the second enclosure 408 to pass between the second enclosure and a tube 414 (illustrated at 420). The tube 414 connected to the second enclosure at a first end of the tube wherein the end of the tube 414 is inserted into the third aperture 407 and the second end of the tube is connected to a central analysis device.

As mentioned above, the chamber 404 includes a valve 410 and when an outflow of air is applied to the valve, the valve restricts movement of air through the chamber. The valve can be a one-way valve with a flap that opens and closes to allow more or less air to enter or exit the chamber through the first aperture 418. This valve can be used in a process to check the system for leaks as will be discussed in more detail below.

In some embodiments, the first aperture 416 in the first enclosure 412 can be comprised of a plurality of smaller apertures (as illustrated in FIGS. 4A and 4B. For example, the side of the body that has its first aperture can be surrounded by a surface of the first enclosure and that surface can be perforated with a number of holes that are smaller than the first aperture, as shown in FIGS. 4A and 4B.

Alternatively, this arrangement can be provided by placing a mesh material over the first aperture. Such an arrangement can provide a protective barrier to reduce blockage of the sample point by objects larger than those that can fit through the smaller apertures, while allowing air to pass through the aperture between the area to be sample and the chamber.

As discussed above and illustrated in the embodiment of FIGS. 4A and 4B, the body can be connected to the first enclosure. For example, in some embodiments, the first enclosure 412 includes a nozzle 409 formed inside the enclosure and the body 402 is connected to the nozzle 409.

In some embodiments, the body can be replaceably connected to the nozzle, allowing for the first enclosure to be opened, (e.g., removal of one of the sides of the first enclosure) the body removed, and a new body can be connected to the nozzle by placement of the second aperture of the body 402 over the outer surface of the nozzle 409.

Alternatively, the body can be fixedly attached to the nozzle, for example, in unitary designs, where replacement of the sample point would include replacement of a unit including the body and combination of one or both of the first and second enclosures.

FIG. 4A illustrates when the sample point is in normal operation. In this example, air flows from the area to be sampled 406 into the first enclosure 412, via aperture 416, and then into chamber 404, via aperture 418. The air drawn in through the apertures 416 and 418 pushes the flap on valve 410 open as it passes into the chamber 404 of the body 402.

The air is then drawn out of the chamber 404 and into an area 408 within the second enclosure 413 (e.g., between the materials forming the first and second enclosures). As used herein, the area 408 is the entire space between the first enclosure and the second enclosure.

The air 420 is, further, drawn from the area 408 in the second enclosure into the tube 414 and to the central analysis device. To accomplish this, the central analysis device includes a reversible pump that draws air from the sample point to the central analysis device or reverses to push air to the sample point, for cleaning and leak checking, for example.

In order to test to see if the system needs to be cleaned, the central analysis device can compare air pressure values of the air currently being drawn through the tube 414 and a threshold valve stored in memory, either on the central analysis device or stored remotely. Although not shown in the drawings, an example of one suitable central analysis device is the central detector unit of the VESDA E VEA system manufactured by Honeywell.

Figure 5:
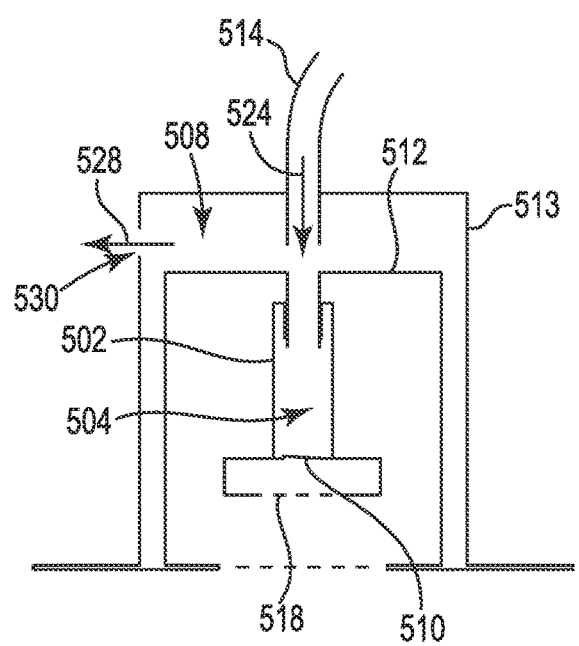
FIG. 5 illustrates a cutaway side view of a sample point according to an embodiment of the present disclosure wherein the valve is in a closed (outflow) position and there is a breach in the outer enclosure.
Figure 6:
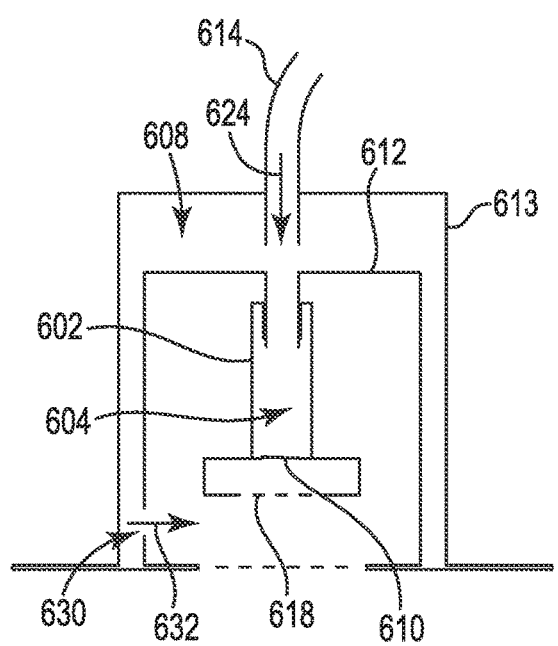
FIG. 6 illustrates a cutaway side view of a sample point according to an embodiment of the present disclosure wherein the valve is in a closed (outflow) position and there is a breach in the inner enclosure.

FIG. 4B illustrated a leak checking operation where the reversed air is pushed out of the tube 414 and into the second enclosure 413. Since there are no breaches in the second enclosure 413 creating a leak, the air is then pushed through the second aperture in the first enclosure 412 and into chamber 404. The air pushes the flap of the valve 410 closed, restricting the passing of air out of the chamber (as indicted at 420 in FIG. 4B). In doing so, the air pressure will rise and this current air pressure and associated outward flow reading can be compared by the central analysis device with an expected flow and pressure to determine whether a leak is present in the system. FIGS. 5 and 6 illustrate examples where leaks are present in the system.

Specifically, FIG. 5 illustrates a cutaway side view of a sample point according to an embodiment of the present disclosure wherein the valve is in a closed (outflow) position and there is a breach in the outer enclosure. FIG. 5 illustrates an embodiment similar to that shown in FIGS. 4A and 4B, but wherein the second enclosure has a breach in a side surface allowing air 528 to flow between the interior of the second enclosure and the area above the ceiling.

In this example, a leak test is being performed (as indicated by the outflow of air 524 from tube 514 into the area 508 within the second enclosure 513). The air also is pushed into the chamber 504 of the body 502 through the second aperture in the body and second aperture in the first enclosure 512 and closes the valve 510. Because the valve 510 is in the closed position, the pressure in the system should be higher, as the air flow out of the first aperture 518 of the body is restricted.

However, the air 528, instead, flows out of the breach 530, and thereby, the pressure may not rise above the threshold level or the air flow exceeds an expected value when the central analysis device tests the system. This would indicate to the central analysis device that there is a breach in the system.

FIG. 6 illustrates a cutaway side view of a sample point according to an embodiment of the present disclosure wherein the valve is in a closed (outflow) position and there is a breach in the inner enclosure. Similarly, FIG. 6 illustrates an embodiment similar to that shown in FIGS. 4A and 4B, but wherein the first enclosure 612 has a breach 630 in a side surface allowing air 632 to flow between the interior of the second enclosure 613 and the first enclosure, but not through the chamber 604 and past the valve 610 of the body 602.

In this example, a leak test is, again, being performed (as indicated by the outflow of air 624 from tube 614 into the area 608 within the second enclosure 613. Again, in this example, because the valve 610 is in the closed position, the pressure in the system should be higher, as the air flow out of the first aperture 618 of the body is restricted.

Instead, the air 632 flows through the breach 630, and thereby, the pressure may not rise above the threshold level when the central analysis device compares the air pressures. This would, also, indicate to the central analysis device that there is a breach in the system.

As can be understood from the above discussion, the embodiments of the present disclosure provide significant benefits with regard to leak detection for smoke detection systems using sample points as well as providing a protective type enclosure that is useful in some applications. These benefits include earlier, more accurate smoke detection, which can save property and, in some cases, the lives of the occupants of the area being sampled, among other benefits.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion and not a restrictive one. Combination of the above embodiments, and other embodiments not specifically described herein, will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A smoke detection sample point, comprising:
   a body;
      a first chamber formed within the body, the first chamber having a first aperture, to allow air to pass between an area to be sampled and the first chamber, and a second aperture, to allow air to pass between the first chamber and a second chamber within a second enclosure;
      a valve positioned within the first chamber;
   a first enclosure having a third chamber surrounding the body, but allowing the first aperture to pass air between the area to be sampled and the first chamber and the second aperture to pass air between the first chamber and the second chamber within the second enclosure; and
   the second chamber of the second enclosure surrounding the first enclosure and having a third aperture, the third aperture allowing the air in the second chamber within the second enclosure to pass between the second enclosure and a tube connected to the second enclosure.

2. The smoke detection sample point of claim 1, wherein the valve is a one-way valve.

3. The smoke detection sample point of claim 1, wherein when an outflow of air is applied to the valve, the valve restricts movement of air through the first chamber.

4. The smoke detection sample point of claim 1, wherein the tube is connected to the second enclosure at a first end of the tube and connected at second end of the tube to a central analysis device.

5. The smoke detection sample point of claim 1, wherein the tube is connected to the second enclosure at a first end of the tube.

6. The smoke detection sample point of claim 1, wherein the tube is connected to the second enclosure at a first end of the tube and wherein the first end of the tube is inserted into the third aperture of the second enclosure.

7. The smoke detection sample point of claim 1, wherein the first aperture includes a protective mesh material thereon.

8. The smoke detection sample point of claim 1, wherein the body is connected to the first enclosure.

9. The smoke detection sample point of claim 1, wherein the valve includes a flap that opens and closes to restrict the amount of air passing through the valve.

10. A smoke detection sample point, comprising:
    a body;
       a first chamber formed within the body, the first chamber having a first aperture, to allow air to pass between an area to be sampled and the first chamber, and a second aperture, to allow air to pass between the first chamber and a second chamber within a second enclosure;
       a valve positioned within the first chamber;
    a first enclosure having a third chamber surrounding the body, but allowing the first aperture to pass air between the area to be sampled and the first chamber and the second aperture to pass air between the first chamber and the second chamber within the second enclosure; and
    the second chamber of the second enclosure surrounding the first enclosure and having a third aperture, the third aperture allowing the air in the second chamber within the second enclosure to pass between the second enclosure and a tube, connected to the second enclosure at a first end of the tube and connected at second end of the tube to a central analysis device.

11. The smoke detection sample point of claim 10, wherein the first enclosure includes a nozzle formed inside the enclosure and wherein the body is connected to the nozzle.

12. The smoke detection sample point of claim 10, wherein the first enclosure includes a nozzle formed inside the enclosure and wherein the body is replacably connected to the nozzle.

13. The smoke detection sample point of claim 10, wherein the first enclosure includes a nozzle formed inside the enclosure and wherein the body is connected to the nozzle.

14. A smoke detection sample point, comprising:
   a body;
      a first chamber formed within the body, the first chamber having a first aperture, to allow air to pass between an area to be sampled and the first chamber, and a second aperture, to allow air to pass between the first chamber and a second chamber within a second enclosure;
      a one-way valve positioned within the first chamber that allows inflow of air from the area to be sampled and restricts the outflow of air from the first chamber;
   a first enclosure having a third chamber surrounding the body, but allowing the first aperture to pass air between the area to be sampled and the first chamber and the second aperture to pass air between the first chamber and the second chamber within the second enclosure; and
   the second chamber of the second enclosure surrounding the first enclosure and having a third aperture, the third aperture allowing the air in the second chamber within the second enclosure to pass between the second enclosure and a tube connected to the second enclosure, connected to the second enclosure at one end and connected at its other end to a central analysis device.

\* \* \* \* \*